US009463193B2

(12) United States Patent
Gamelin et al.

(10) Patent No.: US 9,463,193 B2
(45) Date of Patent: *Oct. 11, 2016

(54) INDIVIDUAL 5-FLUOROURACILE DOSE OPTIMIZATION IN FOLFIRI TREATMENT (75) Inventors: Erick Gamelin, Bouchemaine (FR); Michéle Boisdron-Celle, Saint Leger Des Bois (FR); Alain Morel, Juigne Sur Loire (FR)

(73) Assignees: INSTITUT DE CANCEROLOGIE DE L'OUEST, Angers (FR); UNIVERSITE D'ANGERS, Angers (FR)

( * ) Notice: Subject to any disclaimer, the term of this patent is extended or adjusted under 35 U.S.C. 154(b) by 773 days.

This patent is subject to a terminal disclaimer.

(21) Appl. No.: 13/121,103

(22) PCT Filed: Sep. 26, 2008

(86) PCT No.: PCT/IB2008/055626
§ 371 (c)(1),
(2), (4) Date: Mar. 25, 2011

(87) PCT Pub. No.: WO2010/035076
PCT Pub. Date: Apr. 1, 2010

(65) Prior Publication Data
US 2011/0177092 A1    Jul. 21, 2011

(51) Int. Cl.
A61K 39/395    (2006.01)
A61K 31/4745   (2006.01)
A61K 31/513    (2006.01)
A61K 31/519    (2006.01)

(52) U.S. Cl.
CPC ......... *A61K 31/513* (2013.01); *A61K 31/4745* (2013.01); *A61K 31/519* (2013.01); *A61K 39/39558* (2013.01)

(58) Field of Classification Search
USPC .................................................... 424/155.1
See application file for complete search history.

(56) References Cited

U.S. PATENT DOCUMENTS

2007/0280944 A1*  12/2007  Robbins et al. ........... 424/155.1
2011/0246079 A1*  10/2011  Gamelin et al. ................ 702/19

FOREIGN PATENT DOCUMENTS

EP         1 712 643 A1    10/2006

OTHER PUBLICATIONS

Tournigand et al. (J Clin Oncol. , 2004, 22: 229-237).*
NCI drug dictionary-fluorouracil.*
Saif et al. (J. Natl Cancer Inst, Nov. 18, 2009, 101(22):1543-52).*

Bocci el al., "A pharmacokinetic-based test to prevent severe 5-fluorouracil toxicity," Clin Pharma & Therapeutics, 2006, pp. 384-395, vol. 80, No. 4.
Bouché et al., "Randomized Multicenter Phase II Trial of a Biweekly Regimen of Fluorouracil and Leucovorin (LV5FU2), LV5FU2 Plus Cisplatin, or LV5FU2 Plus Irinotecan in Patients With PreViously Untreated Metastatic Gastric Cancer: A Fédération Francophone de Cancérologie Digestive Group Study—FFCD 9803," J Clin Oncology, Nov. 2004, pp. 4319-4328, vol. 22, No. 21.
Ciccolini et al., "A simple and rapid high-performance liquid chromatographic (HPLC) method for 5-fluorouracil (5-FU) assay in plasma and possible detection of patients with impaired dihydropyrimidine dehydrogenase (DPD) activity," J Clin Pharma and Therapeutics, 2004, pp. 307-315, vol. 29.
Douillard et al., "Irinotecan combined with fluorouracil.compared with fluorouracil alone as first-line treatment for metastatic colorectal cancer: a multicentre randomised trial," Lancet, Mar. 2000, pp. 1041-1047, vol. 355.
Etienne et al., "Population study of Dihydropyrimidine Dehydrogenase in Cancer Patients," J Clin Oncol, Nov. 1994, pp. 2248-2253, vol. 12, No. 11.
Gamelin et al., "Correlation Between Uracil and Dihydrouracil Plasma Ratio, Fluorouracil (5-FU) Pharmacokinetic Parameters, and Tolerance in Patients With Advanced Colorectal Cancer: A Potential Interest for Predicting 5-FU Toxicity and Determining Optimal 5-FU Dosage," J Clin Oncol, Apr. 1999, 1105-1110, vol. 17, No. 4.
Gamelin et al., "Dose monitoring of 5-fluorouracil in patients with colorectal or head and neck cancer—status of the art," Crit Rev Oncol Hematol, 1999, pp. 71-79, vol. 30.
Gamelin et al., "Individual Fluorouracil Dose Adjustment Based on Pharmacokinetic Follow-Up Compared With Conventional Dosage: Results of a Multicenter Randomized Trial of Patients With Metastatic Colorectal Cancer," J Clin Oncõl., May 2008, pp. 2099-2105, vol. 26, No. 13.
Gamelin et al., "Long-Term Weekly Treatment of Colorectal Metastatic Cancer With Fluorouracil and Leucovorin: Results of a Multicentric Prospective Trial of Fluorouracil Dosage Optimization by Pharmacokinetic Monitoring in 152 Patients," J. Clin. Oncol., Apr. 1998, pp. 1470-1478, vol. 16, No. 4.
Garg et al., "Simple liquid chromatographic method for the determination of uracil and dihydrouracil plasma levels: a potential pretreatment predictor of 5-fluorouracil toxicity," J Chromatography B, 2002, pp. 223-230, vol. 774.
Gary et al., "Epidermal growth factor receptor monoclonal antibodies for the treatment of metastatic colorectal cancer," Pharmacotherapy, Jun. 2008, pp. 742-754, vol. 28, No. 6.

(Continued)

*Primary Examiner* — Yan Xiao
(74) *Attorney, Agent, or Firm* — Foley & Lardner LLP (57) ABSTRACT

The present invention belongs to the field of improved personalized medicine. More precisely, the present invention relates to a method for progressively optimizing the 5-FU dose administered by continuous infusion in patients treated by a FOLFIRI regimen or a similar regimen, based on the 5-FU plasmatic concentration measured during the previous 5-FU continuous infusion and on a herein described decision algorithm. The present invention also relates to a method for treating a cancer patient in which the 5-FU dose administered in continuous infusion in each FOLFIRI or similar treatment cycle is optimized using the decision algorithm according to the invention.

14 Claims, 2 Drawing Sheets

(56) References Cited

OTHER PUBLICATIONS

Kabbinavar et al., "Health-Related Quality of Life Impact of Bevacizumab When Combined with Irinotecan, 5-Fluorouracil, and Leucovorin or 5-Fluorouracil and Leucovorin for Metastatic Colorectal Cancer," The Oncologist, 2008, pp. 1021-1029, vol. 13.

Pinto et al., "Phase II study of cetuximab in combination with FOLFIRI in patients with untreated advanced gastric or gastroesophageal junction adenocarcinoma (FOLCETUX study)," Annals of Oncol, Mar. 2007, pp. 510-517, vol. 18, No. 3.

Rouits et al., "Relevance of Different UGT1A1 Polymorphisms in Irinotecan-Induced Toxicity: A Molecular and Clinical Study of 75 Patients," Clin Cancer Res., Aug. 2004, pp. 5151-5159, vol. 10, No. 15.

Vanhoefer et al., "Irinotecan in the Treatment of Colorectal Cancer: Clinical Overview," J. Clin. Oncol., Mar. 2001, pp. 1501-1518, vol. 19, No. 5.

Ychou et al., "Individual 5-FU dose adaptation in metastatic colorectal cancer: results of a phase II study using a bimonthly pharmacokinetically intensified LV5FU2 regimen," Cancer Chemother Pharmacol, 2003, pp. 282-290, vol. 52.

\* cited by examiner

INDIVIDUAL 5-FLUOROURACILE DOSE OPTIMIZATION IN FOLFIRI TREATMENT

The present invention belongs to the field of improved personalized medicine. More precisely, the present invention relates to a method for progressively optimizing the 5-FU dose administered by continuous infusion in patients treated by a FOLFIRI regimen or a similar regimen, based on the 5-FU plasmatic concentration measured during the previous 5-FU continuous infusion and on a herein described decision algorithm. The present invention also relates to a method for treating a cancer patient in which the 5-FU dose administered in continuous infusion in each FOLFIRI or similar treatment cycle is optimized using the decision algorithm according to the invention.

BACKGROUND ART

Most drugs may have deleterious effects. However, anticancer drugs are among those resulting in the worse adverse effects. Indeed, anticancer drugs are usually cytotoxic active agents with some preference for tumor cells. However, they also display some toxicity on other cells, thus resulting in often serious adverse reactions (20-25% of grade 3-4 toxicity and 0.2% mortality).

This is an important problem, since serious adverse effects not only affect patients' life quality, but may also result in death due to toxicity, or more often to the end or decrease of the treatment, thus decreasing its efficiency.

Interindividual metabolism variations, which influence drugs anabolism and catabolism capacities, participate to the toxicity risk. However, despite some recent improvements of the knowledge concerning anticancer drugs metabolism and of pharmacological technologies, therapeutic individualization is not yet common practice.

In contrast, doses are usually standardized. Although doses and protocols standardization may have been once useful, it now shows its limits concerning efficiency and toxicity of the treatment, depending on the treated subject.

However, the administered dose of anticancer drug is usually still calculated depending on body surface, which relevancy is based neither on experimental or theoretical justification, and at best on a few biological tests such as complete blood count and renal check-up. Individual pharmacokinetic, metabolic, genetic or epigenetic particularities are not taken into account.

There is thus a need for treatment methods using anticancer compounds in which such individual particularities would be taken into account in order to decrease toxicity and improve efficiency of the treatment.

5-fluorouracile (5-FU) is the leading anticancer drug of fluoropyrimidine family, a therapeutic class of agents interfering with DNA synthesis. 5-FU is a major chemotherapeutic drug, and is notably used in the treatment of colorectal cancer, gastric cancer, oesophagi cancer, ORL cancer, and breast cancer, particularly as an adjuvant treatment or in metastatic situations. Each year, more than 90 000 patients are treated by 5-FU.

However, 5-FU results in 20-25% of severe grade 3-4 toxicity, including toxicities in the digestive tract, such as diarrhea, which may be bloody or hemorrhagic; haematopoietic complications, such as leuco-neutropenias, which may result in superinfection or septicaemia; skin or mucosa complications, such as mucites, hand-foot syndrome; toxidermia; cardiac toxicity and a cerebellum syndrome.

Such adverse effects may be combined with each other, resulting in a polyvisceral toxicity scheme, with is very early in 5-8% of patients and even gives rise to death in 0.8% of treated patients. These adverse effects may also appear later, during the treatment.

5-FU is usually used in metastatic situations. In addition, it is also more and more often used as an adjuvant treatment, i.e. in the case of patients treated for a localized tumor for which a relapse is feared. The risk of a severe toxic adverse effect cannot be taken in such conditions.

The adverse effects of 5-FU are mainly due to a great interindividual variability of 5-FU metabolism. 5-FU cytotoxicity mechanism is based on its conversion in active nucleotides that block DNA synthesis. Such active nucleotides are obtained when 5-FU is metabolised by the anabolic pathway. However, there is an equilibrium between 5-FU enzymatic activation (anabolic pathway) and 5-FU elimination in the catabolic pathway. The initial and limiting enzyme of 5-FU elimination (catabolic pathway is dihydropyrimidine dehydrogenase (DPD). This ubiquitous enzyme is a major factor of 5-FU biodisponibility, since in a subject with normal DPD enzymatic activity, about 80% of administered 5-FU is eliminated by DPD in the catabolic pathway, while only 20% of administered 5-FU is available for the anabolic pathway that us necessary for its cytotoxic action.

However, in patients with a deficiency (total or partial) in DPD activity, the percentage of administered 5-FU that is available for the anabolic pathway that is necessary for its cytotoxic action is greatly increased, and these patients thus have an increased risk of developing acute, early and severe 5-FU toxicity.

On the other hand, in patient with an increased DPD activity a standard dose based on the body surface area is insufficient and consequently inefficient.

DPD activity shows a great interindividual variability, with measured activity values that may differ from a 6 times ratio between two distinct patients (Etienne M C, et al: J Clin Oncol 12: 2248-2253, 1994). This enzymatic variability results in a great variability in 5-FU metabolism and plasmatic kinetics, since 5-FU clearance varies of a factor 6 to 10 depending on the subject (Gamelin E., et al. J Clin Oncol, 1999, 17, 1105-1110; Gamelin E., et al. J. Clin. Oncol., 1998, 16 (4), 1470-1478).

This situation has enormous implications for treatment toxicity, but also for treatment efficiency. Indeed, several studies have shown that pharmacokinetic parameters are correlated with toxicity but also with treatment efficiency, notably concerning tumor response in colorectal and ORL cancers.

In addition, it has been found that the range of plasmatic 5-FU concentration in which the treatment is efficient and does not lead to severe adverse effects is rather narrow, so that there is not much difference between efficient and toxic plasmatic 5-FU concentrations.

There is thus a need for treatment methods that would take such variability into account in order to administer to each patient a 5-FU dose that will result in a plasmatic 5-FU concentration in the narrow range in which it is both sufficient to have therapeutic activity and is low enough to prevent severe grade 3-4 toxicities.

In addition to DPD activity variability, 5-FU metabolism also highly depends on the administered dose and mostly on administration duration, i.e. on perfusion duration. Indeed, DPD is saturable, so that a patient's plasmatic kinetics is not linear, and clearance is multiplied by a factor 10 when changing from a bolus administration to a continued perfusion during several hours or days (Gamelin E., Boisdron-Celle M. Crit Rev Oncol Hematol, 1999, 30, 71-79).

A general individual optimization method of 5-FU dose cannot thus be provided. In contrast, although some tolerance may apply for small variations, a particular individual optimization method of 5-FU dose has to be found for each 5-FU treatment protocol, depending on the dose and mostly duration of 5-FU administration.

In addition, the increase or decrease in 5-FU plasmatic concentration in a patient is not proportional to the increase or decrease of the dose of 5-FU that is administered to said patient, so that it is not easy to determine how much to increase or decrease the administered 5-FU dose in order to reach a particular 5-FU plasmatic concentration when starting from a higher or lower concentration obtained with a given administered 5-FU dose.

Moreover, although 5-FU was at some time used in monotherapies, it is now usually administered in combination with other cytotoxic agents, such as oxaliplatine or irinotecan, and optionally with additional targeted therapies using monoclonal antibodies, such as cetuximab, panitumumab or bevacizumab.

These additional agents, and particularly chemotherapeutic agents such as oxliplatin or irinotecan, may also generate adverse effects, which may be similar to those induced by 5-FU, thus creating a risk of synergism in toxicity development as well as in tumor treatment.

In particular, irinotecan may notably induce acute diarrhea, neutropenia and thrombopenia (Vanhoefer, U et al. J. Clin. Oncol., 19: 1501-1518, 2001).

As a result, depending on the chemotherapeutic agent that is used in combination with 5-FU, a particular individual optimization method of 5-FU dose has to be found. Such a method should determine the range in which the 5-FU plasmatic concentration is used.

Some attempts to optimize the 5-FU dose administered to patients in anticancer protocols have been made. However, as mentioned above, results are not transposable to other protocols, in particular if the administration mode (and notably the duration of the continuous infusion) of 5-FU is changed, or if 5-FU is combined with a chemotherapeutic agent that may influence 5-FU pharmacokinetics such as oxaliplatin.

Gamelin et al (Gamelin, E et al. J Clin Oncol. 2008 May 1; 26(13):2099-105) defined a method for adapting 5-FU dose in a treatment based on weekly administration of folinic acid combined with 5-FU in an 8 hours continuous infusion. However, such a protocol is no more used, since current protocols generally combine 5-FU with folinic acid and another chemotherapeutic drug, generally oxaliplatin or irinotecan. In addition, current protocols use much longer continuous infusions of 5-FU.

Ychou et al (Ychou M, Duffour J, Kramar A, et al. Cancer Chemother Pharmacol, 2003, 52: 282-90.) describe a method for increasing 5-FU dose in a treatment based on a bimonthly LV5FU2 regimen. However, such a protocol is also no more used, since current protocols generally combine 5-FU with folinic acid and another chemotherapeutic drug, generally oxaliplatin or irinotecan. In addition, the method described in Ychou et al only intends to increase the 5-FU dose, and an increase is systematically applied unless a significant (grade II-IV) toxicity is observed. Thus, although this method permits to increase the 5-FU dose and potentially to increase treatment efficiency, it does not permit to prevent severe toxicity by remaining in the narrow window in which 5-FU plasmatic levels are efficient but not toxic. The method of Ychou et al thus still make the patient take a significant risk, which is not acceptable in first line treatment.

In the present application, the inventors have found a method for optimizing the next 5-FU dose to be administered by continuous infusion to a patient treated with a FOLFIRI protocol (5-FU in bolus and continuous infusion of 46 hours, folinic acid, and irinotecan), based on the plasmatic 5-FU concentration measured from a blood sample taken before the end of the 5-FU perfusion, and on a new decision algorithm.

DESCRIPTION OF THE INVENTION

The present invention thus concerns a method for determining from a blood sample of a patient suffering from cancer the dose $D(n+1)$ of 5-fluorouracile (5-FU) for the next cycle of treatment $(n+1)$, wherein
  each treatment cycle i comprises:
    0-500 mg/m$^2$ of 5-fluorouracile (5-FU) administered in a bolus,
    0-600 mg/m$^2$ of folinic acid or a salt thereof,
    a dose $D(i)$ (in mg/m$^2$) of 5-FU administered in a continuous infusion of 43 to 49 hours, and
    0-500 mg/m$^2$ of irinotecan; and
  said blood sample has been taken from said patient in previous treatment cycle n at least 2 hours after the beginning of the 5-FU perfusion and before the end of said perfusion,
said method comprising:
  dosing in vitro the 5-FU plasmatic concentration ([5-FU]) in the blood sample
  calculating $D(n+1)$ depending on $D(n)$ using the following decision scheme:
    if [5-FU]<100 µg/L, then $D(n+1)=D(n)\times 1.40$,
    if $100\leq$[5-FU]<200 µg/L, then $D(n+1)=D(n)\times 1.30$,
    if $200\leq$[5-FU]<300 µg/L, then $D(n+1)=D(n)\times 1.20$,
    if $300\leq$[5-FU]<400 µg/L, then $D(n+1)=D(n)\times 1.10$,
    if $400\leq$[5-FU]<500 µg/L, then $D(n+1)=D(n)\times 1.05$,
    if $500\leq$[5-FU]<600 µg/L, then $D(n+1)=D(n)\times 1.025$,
    if $600\leq$[5-FU]$\leq 650$ µg/L, then $D(n+1)=D(n)$,
    if $650<$[5-FU]<700 µg/L, then $D(n+1)=D(n)\times 0.975$,
    if $700\leq$[5-FU]<800 µg/L, then $D(n+1)=D(n)\times 0.95$,
    if $800\leq$[5-FU]<900 µg/L, then $D(n+1)=D(n)\times 0.90$,
    if $\geq 900$ [5-FU], then $D(n+1)=D(n)\times 0.80$.

The present invention also relates to a method for treating a patient suffering from cancer, comprising:
  Administering to said patient successive treatment cycles, in which each treatment cycle i comprises:
    0-500 mg/m$^2$ of 5-fluorouracile (5-FU) administered in a bolus,
    0-600 mg/m$^2$ of folinic acid or a salt thereof,
    a dose $D(i)$ of 5-FU (in mg/m$^2$) administered in a perfusion of about 46 hours, and
    0-500 mg/m$^2$ of irinotecan.
  At each cycle i, taking a blood sample from the patient at least 3 hours after the beginning of the 5-FU perfusion and before the end of said perfusion, and dosing in vitro the 5-FU plasmatic concentration ([5-FU]), wherein
  the initial dose $D(1)$ at treatment cycle 1 is at most 2500 mg/m$^2$
  at each cycle i, the next dose $D(i+1)$ of the next treatment cycle $i+1$ is determined using the following decision scheme:
    if [5-FU]<100 µg/L, then $D(n+1)=D(n)\times 1.40$,
    if $100\leq$[5-FU]<200 µg/L, then $D(n+1)=D(n)\times 1.30$,
    if $200\leq$[5-FU]<300 µg/L, then $D(n+1)=D(n)\times 1.20$,
    if $300\leq$[5-FU]<400 µg/L, then $D(n+1)=D(n)\times 1.10$,
    if $400\leq$[5-FU]<500 µg/L, then $D(n+1)=D(n)\times 1.05$,
    if $500\leq$[5-FU]<600 µg/L, then $D(n+1)=D(n)\times 1.025$, if 600≤[5-FU]≤650 µg/L, then D(n+1)=D(n),
if 650<[5-FU]<700 µg/L, then D(n+1)=D(n)×0.975,
if 700≤[5-FU]<800 µg/L, then D(n+1)=D(n)×0.95,
if 800≤[5-FU]<900 µg/L, then D(n+1)=D(n)×0.90,
if ≥900 [5-FU], then D(n+1)=D(n)×0.80.

The methods according to the invention thus concern cancer patients treated by a FOLFIRI regimen or a similar regimen.

The above described decision algorithm has been developed and tested on cancer patients following a FOLFIRI regimen:

FOLFIRI (Douillard, J. Y., et al: Lancet 355: 1041-1047, 2000): a cycle every 15 days, comprising:
5-FU bolus 400 mg/m$^2$
+elvorine (calcium folinate, 100 mg/m$^2$) at day 1
+5-FU 46 hours (initial dose D(1)=2500 mg/m$^2$ or less if the patient has an increased sensitivity to 5-FU, see below) starting on day 1 and stopping on day 2
+180-250 mg/m$^2$ of irinotecan at day 1

As mentioned in the background section, algorithms for optimizing 5-FU dose cannot be transposed from a particular treatment regimen to another really different specific treatment regimen.

Since the above described algorithm has been elaborated and tested on cancer patients treated with FOLFIRI regimen (see above), it is accurate for these particular regimens and for similar regimens. Indeed, parameters such as the duration of the 5-FU continuous infusion, the presence of folinic acid or of irinotecan cannot be significantly changed. However, a small variation in these parameters does not impair the accuracy of the decision algorithm.

Regimens similar to FOLFIRI regimen can thus be defined as regimens comprising repeated treatment cycles, two successive cycles being separated by about two weeks (cycles are separated by two weeks in normal cases. However, in case of significant toxicity observed after a particular cycle, the next cycle may be delayed of about one or several weeks, thus separating the two cycles of about three weeks or more), each treatment cycle comprising:
0-500 mg/m$^2$ of 5-fluorouracile (5-FU) administered in a bolus,
0-600 mg/m$^2$ of folinic acid or a salt thereof,
a dose D(i) (in mg/m$^2$) of 5-FU administered in a continuous infusion of 43 to 49 hours, and
0-500 mg/m$^2$ of irinotecan.

Each cycle i is preferably identical to the previous cycle (i−1), except for the 5-FU dose D(i) administered in a continuous infusion, which is optimized based on the plasmatic 5-FU concentration measured from said patient blood sample taken during the 5-FU continuous infusion of the previous cycle and on the above described decision algorithm.

As mentioned before, the duration of the 5-FU continuous infusion may not be significantly changed compared to the 46 hours of the FOLFIRI protocols. However, a 5-10% variation does not impair the algorithm accuracy, and the duration of the 5-FU continuous infusion may thus be comprised between 43 and 49 hours. In preferred embodiments, the duration of the 5-FU continuous infusion is however comprised between 44 and 48 hours, preferably 45 to 47 hours, and most preferably is about 46 hours. According to the invention, the term "about", when applied to a time period, is intended to mean an increase or decrease of half an hour around the specified value.

The particular treatment regimens on which the above described decision algorithm has been elaborated and tested comprise in each cycle i a 5-FU bolus of 400 mg/m$^2$. However, contrary to the presence of folinic acid or of oxaliplatin in treatment cycles, the presence of a 5-FU bolus is not a critical parameter for the accuracy of the decision algorithm.

Indeed, when it is present, the 5-FU bolus is administered before the beginning of the 5-FU continuous infusion. Usually, when a 5-FU bolus is administered, then the 43-49 hours 5-FU infusion is just following the 5-FU bolus. In addition, 5-FU has a very short half-life in blood, and 5-FU plasmatic concentration thus very rapidly decrease after the end of the 5-FU bolus, so that the 5-FU bolus dose does not affect the 5-FU plateau plasmatic concentration during the continuous infusion and has thus no influence on the decision algorithm, provided however that the 5-FU bolus dose does not exceed 500 mg/m$^2$. However, in preferred embodiments, each treatment cycle i is such that a dose of 5-FU of about 400 mg/m$^2$ is administered in a bolus, as in known FOLFIRI regimens.

In all the present invention, the term "about", when applied to any therapeutic agent dose (including 5-FU, folinic acid, and oxaliplatin), is intended to mean an increase or decrease of 10% around the specified value.

As mentioned before, folinic acid is necessarily present in each treatment cycle i. Folinic acid, i.e. N-(5-formyl-(6R, S)-5,6,7,8-tetrahydropteroyl)-L-glutamic acid, when obtained by chemical synthesis, is formed by an equimolar mixture of its two (6R) (also called D-folinic acid because this isomer is dextrogyre) and (6S) (also called L-folinic acid because this isomer is levogyre) diastereomeric forms. It is known that only the (6,S) isomer, has the well-known pharmacological activity of the product, while the other one is totally devoid of it. In all the present application, although folinic acid or a salt thereof may be administered as a racemate mixture of L- and D-folinic acid, any dose of folinic acid or salt thereof is thus expressed as a dose of L-folinic acid. Thus, when a range of 0-600 mg/m$^2$ of folinic acid is mentioned, then it means that a dose of 0-600 mg/m$^2$ of L-folinic acid is administered to the patient. As a result, if a racemate mixture of L- and D-folinic acid is administered, then the total (L- and D-folinic acid) dose of folinic acid is comprised between 0-1200 mg/m$^2$ so that the dose of L-folinic acid be comprised between 0-600 mg/m$^2$.

In the particular treatment regimens on which the above described decision algorithm has been elaborated and tested, the dose of folinic acid (i.e. the dose of L-folinic acid) is 100 mg/m$^2$. The decision algorithm can thus be relevant for a dose of 0-600 mg/m$^2$. In preferred embodiment, the dose of folinic acid administered in each cycle i is comprised between 24-360 mg/m$^2$, preferably 45-240 mg/m$^2$, more preferably 56-180 mg/m$^2$, even more preferably 80-120 mg/m$^2$. Most preferably, the dose of folinic acid administered in each cycle i is about 100 mg/m$^2$, as in known FOLFIRI regimen.

As mentioned before, irinotecan is also necessarily present in each treatment cycle i. Since the above described decision algorithm has been elaborated and tested a FOLFIRI regimen with distinct amounts of irinotecan, the decision algorithm can be generalized to any treatment regimen with the above described parameters and with an irinotecan dose administered in each cycle comprised between 0-500 mg/m$^2$, preferably between 100 and 350 mg/m$^2$, preferably between 120 and 300 mg/m$^2$.

In addition, the decision algorithm according to the invention has been further validated in patients treated with a FOLFIRI regimen to which is added the administration of a monoclonal antibody (cetuximab or panitumumab) directed to EGFR (epidermal growth factor receptor), or a monoclonal antibody (bevacizumab) directed to VEGF (vascular endothelial growth factor). Thus, in a further embodiment of the method according to the invention described above, the treatment further comprises in each cycle i the administration to the patient of a anticancer monoclonal antibody, preferably a monoclonal antibody directed to EGFR or VEGF, preferably cetuximab, panitumumab or bevacizumab.

In the present application, "D(i)" always refers to the 5-FU dose administered to the patient at cycle i in a continuous infusion of 43 to 49 hours. The determination of the next dose D(n+1) to be administered at cycle (n+1) depends on the previous dose D(n) administered at cycle n, and on the value of the 5-FU plasmatic concentration ([5-FU]) measured from a patient blood sample taken during the 5-FU continuous infusion of previous cycle n. To be representative, the measured 5-FU plasmatic concentration has to be a plateau 5-FU plasmatic concentration.

5-FU has a very short half-life in blood, and 5-FU plasmatic concentration thus very rapidly decrease after the end of the 5-FU continuous infusion. As a result, to be representative, the blood sample taken from the patient in previous cycle n has to be taken before the end of the continuous infusion, and not after.

In addition, 5-FU plasmatic levels normally reach a plateau about 1 hour after the beginning of the 5-FU continuous infusion. For more security, it is sometimes considered that waiting for 1 hour and a half after the beginning of the 5-FU continuous infusion permits to be sure that the plateau has been reached by most patients. As a result, the blood sample may be taken at least 1 hour, preferably at least 1 hour and a half and even more preferably at least 2 hours after the beginning of the continuous infusion and before the end of said continuous infusion.

However, in some patients, the time necessary to reach a 5-FU plasmatic concentration plateau is higher. Thus, in a preferred embodiment, the blood sample is taken in previous cycle n in the second half of the 5-FU continuous infusion. Advantageously, the blood sample has thus been taken in cycle n 15 minutes to 22 hours, preferably 30 minutes to 10 hours, more preferably 1 hour to 5 hours, and most preferably 2 to 3 hours before the end of the 5-FU continuous infusion.

Alternatively, since the plateau is generally reached about 1 hour after the beginning of the 5-FU continuous infusion, it may be beneficial for other aspects to take the blood sample for pharmacokinetics analysis in the plateau as soon as possible after the beginning of the 5-FU continuous infusion, i.e. as soon as possible after at least 1 hour, preferably at least 1 hour and a half and even more preferably 2 hours after the beginning of the continuous infusion. Indeed, the continuous infusion is for about 46 hours, and patients usually wish to stay the shortest time possible in the hospital. While the set up of the 5-FU continuous infusion should be done by a qualified person in the hospital, there are currently delivery devices that may then permit to the patient to go home and stay at home during the rest of the continuous infusion. This would then permit to significantly improve patients' quality of life, provided that the blood sample necessary for pharmacokinetics analysis and calculation of the next 5-FU dose by continuous infusion be taken before the patient leaves the hospital.

Since 5-FU plasmatic levels normally reach a plateau about 1 hour after the beginning of the 5-FU continuous infusion, in another preferred embodiment, the blood sample is taken in previous cycle n at least 1 hour after the beginning of the 5-FU continuous infusion and but in the first half of the continuous infusion, i.e. between 1 hour and 23 hours after the beginning of the 5-FU continuous infusion, preferably between 1 hour and a half and 10 hours after the beginning of the 5-FU continuous infusion, preferably between 1 hour and a half and 5 hours after the beginning of the 5-FU continuous infusion, preferably between 1 hour and a half and 3 hours after the beginning of the 5-FU continuous infusion, or between 2 hours and 5 hours after the beginning of the 5-FU continuous infusion, preferably between 2 hours and 4 hours or between 2 hours and 3 hours after the beginning of the 5-FU continuous infusion.

In the regimens of cancer patients, an initial 5-FU dose D(1) has to be administered in a continuous infusion of 43-49 hours in cycle 1. This dose is normally fixed to a standard dose of about 2500 mg/m$^2$ (which is the standard dose used in FOLFIRI regimen), except in cases in which the patient has been determined to display an increased sensitivity to 5-FU.

By "increased sensitivity to 5-FU" is meant an increase in said subject, compared to a control subject, of the percentage of 5-FU that is metabolized by the anabolic pathway. In a "control subject", 20% of administered 5-FU is metabolized by the anabolic pathway. In a patient with an increased sensitivity to 5-FU, this percentage is increased and preferably at least 40%, at least 60%, at least 80%, at least 90%, or at least 95% of administered 5-FU is metabolized by the anabolic pathway.

In the case of a patient with an increased sensitivity to 5-FU, the initial dose D(1) is decreased, and the decision algorithm is then applied in the same manner. This way, there is no risk of high grade toxicity, and only benign grade I toxicities should be obtained at worse. The method according to the invention using the decision algorithm then permits to optimize the 5-FU dose D(i) at each cycle in order to reach the maximal tolerable dose.

Thus, the patient has preferably been subjected to the diagnosis of increased 5-FU sensitivity before the beginning of the treatment, and the initial dose D(1) is determined depending on the obtained diagnosis.

In a preferred embodiment of the method according to the invention, the 5-FU dose D(1) administered in a continuous infusion in cycle 1 is at most about 2500 mg/m$^2$ and has been determined based on the pre-treatment diagnosis of a possible increased sensitivity of said patient to 5-FU.

EP 1 712 643 application relates to methods for diagnosing an increased sensitivity to 5-FU of a subject and is herein incorporated by reference it is entirety.

Briefly, the diagnosis of increased sensitivity of said patient to 5-FU is preferably performed from at least one biological sample of said patient by combining at least two of the following in vitro tests:
  a) the analysis of the presence of a significant mutation in DPD gene,
  b) the measure of uracil plasmatic concentration, and
  c) the measure of the ratio dihydrouracil plasmatic concentrations/uracil plasmatic concentration (UH$_2$/U ratio).

By a "biological sample" is meant any sample taken from the patient, including a blood sample, an organ sample (a biopsy for instance), a bone marrow sample, etc. For measuring the uracil and dihydrouracil plasmatic concentrations, said biological sample is preferably a blood or plasma sample. For the analysis of the presence of a significant mutation in DPD gene, said sample may be any biological sample from said patient comprising nucleated cells, including a blood sample, an organ sample (for instance cells isolated from a partially metastased lymph node taken from said patient). Preferably, in all cases, said biological sample is a blood or plasma sample.

A "mutation" in DPD gene means any modification of the nucleic sequence of DPD gene, including substitutions (transversions as well as transitions), deletions and insertions.

A "significant mutation" in DPD gene is defined as a mutation that generates a decrease of DPD enzymatic activity. Preferably, a significant mutation in DPD gene results in a decrease of DPD enzymatic activity of at least 50%, at least 60%, at least 70%, at least 80%, or at least 90% of DPD enzymatic activity. Such mutations are known to skilled artisan. Notably, the mutations in DPD gene of following Table 1 are considered as significant mutations of the DPD gene

TABLE 1

Known significant mutations in DPD gene

| Mutation | Position in DPD gene | Consequence at DPD gene level | Consequence at DPD protein level |
|---|---|---|---|
| R21Stop (=C61T) | exon 2 | Substitution of cytosine by thymine in position 61 | Early stop codon => no DPD activity |
| Del TCAT295 | exon 4 | Deletion of 4 bases in position 295 | Early stop codon => no DPD activity |
| L155Stop (=T464A) | exon 5 | Substitution of thymine by adenine in position 464 | Early stop codon => no DPD activity |
| Del T812 | exon 8 | Deletion of thymine in position 812 | Early stop codon => no DPD activity |
| Del TG1039 | exon 10 | Deletion of 4 bases in position 1039 | Early stop codon => no DPD activity |
| E386Stop (=G1156T) | exon 11, codon 386 | Substitution of guanine by thymine in position 1156 | Early stop codon => no DPD activity |
| I560S (=T1679G) | exon 13, | Substitution of thymine by guanine in position 1679 | conformational change => partial or complete loss of DPD activity |
| Del C1897 | exon 14 | Deletion of cytosine in position 1897 | stop codon at the DPD substrate binding site => complete loss in DPD activity in a patient |
| IVS14 + 1G > A | intron 14 | Substitution of guanine by adenine at intron beginning | complete deletion of exon 14 during pre-messenger RNA transcription (loss of 165 bp) => complete loss of DPD activity |
| D949V (=A2846T) | exon 22 | Substitution of adenine by thymine in position 2846 | Direct interference with cofactor binding or electron transport, altered [4Fe—4S] function |

Significant mutations such as those described in Table 1 may be detected from a blood sample using any method known by those skilled in the art. For instance, hybridization probes and assays, microarrays or sequencing may be used.

The uracil and dihydrouracil plasmatic concentrations may be measured from a blood or plasma sample using any technology known to those skilled in the art. Notably, these concentrations may be measured from a blood or plasma sample using HPLC with UV-detection, using a HPLC column with a stationary phase composed of totally porous spherical carbon particles such as Hypercarb™ columns sold by Thermo Electron (Courtaboeuf, France).

Still more preferably, in a method according to the invention including the diagnosis of an increased sensitivity of said patient to 5-FU from at least one biological sample of said patient by combining at least two of in vitro tests, all three in vitro test have been performed and the initial dose D(1) has been determined using the following decision algorithm:

(a) If
  no significant mutation in DPD gene has been detected and uracil plasmatic concentration is less than 15 µg/L, or
  no significant mutation in DPD gene has been detected and uracil plasmatic concentration is at least 15 µg/L but the $UH_2/U$ ratio is at least 6,
  then a standard dose D(1) of 2500 mg/m² is administered to the patient in cycle 1.
(b) In all other cases,
  if $6 \leq UH_2/U$ ratio, then D(1) is 1750 mg/m²
  if $3 \leq UH_2/U$ ratio<6, then D(1) is 1250 mg/m²
  if $1 \leq UH_2/U$ ratio<3, then D(1) is 750 mg/m²
  if $UH_2/U$ ratio<1, then the patient is preferably not treated with 5-FU.

Using such a protocol for detecting patients with increased sensitivity o 5-FU before any 5-FU administration, the initial 5-FU dose D(1) administered in cycle 1 is adapted and no severe toxicity is normally observed. More precisely, using this protocol of early increased sensitivity o 5-FU detection and dose adaptation, no toxicity or only grade 1 toxicities are usually observed after the first treatment cycle.

The above described methods in which the next 5-FU dose administered in a 43-49 hours infusion in the next cycle can then usually by applied without the observation of toxicities of at least grade 2. Since DPD deficiency is really the major factor involved in 5-FU toxicity, the early detection of increased 5-FU sensitivity and the adaptation of the first cycle dose D(1) of 5-FU administered in a 43-49 hours infusion permits to prevent the occurrence of at least grade 2 toxicities in almost all cases. The above described methods according to the invention can thus be applied without any modification in almost all cases.

However, if in very rare cases, toxicities of at least grade 2 are observed, then the following protocol described in Table 2 below may be used depending on the type of observed toxicity:

| Toxicity type | Initial dose(mg/m²/cycle) | |
|---|---|---|
| | 5-FU Bolus | 5-FU 43-49 h continuous infusion |
| (CTCAE V3.0 Grade) | 400 mg/m² day 1 | 2400 mg/m² or less if a increased sensitivity to 5-FU has been detected |
| | 5-FU dose adaptation at cycle 2 (mg/m²/cycle) | |
| Anemia (all grades) | No modification | No modification |
| Nausea and/or vomiting Grade 4 in spite of pre-medication | Adapted anti-emetic therapy Treatment stopped if not tolerable | |
| Neutropenia ou Thrombopenia Grade 3 or 4 Febril Neutropenia defined as fever grade 2 (oral measure ≥38° C. or 3 elevations ≥38° 1 C. in 24 hours), associated to a grade 4 neutropenia. Diarrhea Grade 3 or 4 Stomatitis Grade 3 or 4 | 300 then 200 * | 20% decrease ** |
| Cardiac toxicity ≥ Grade 2 | Treatment stopped | |
| Cutaneous toxicity Grade 3 or 4 | 300 then 200 * | 20% decrease 20% ** |
| Allergy Grade 3 or 4 | Treatment stopped | |
| Neurocérébelleuse | Treatment stopped | |
| Alopecia (all Grades) | No modification | No modification |
| Local tolerance (all Grades) | No modification | No modification |
| Other toxicity clearly linked to a chemo-therapeutic drug | | |
| Grade 1 and 2 | No modification | No modification |
| Grade 3 | 300 then 200 * | 20% decrease ** |
| Grade 4 | Treatment stopped | Treatment stopped |

* 5-FU: In case of hematological toxicity recurrence after two dose reductions, the administration of a 5-FU bolus is stopped.
Folinic acid: folinic acid doses are usually not modified.
** compared to the former 5-FU dose (in mg) administered in the preceding treatment cycle The methods according to the invention are intended for patients suffering from diseases that may be treated using a FOLFIRI regimen or a similar regimen. Such diseases notably include colorectal cancer, stomach cancer, hepatic ducts cancer, pancreas cancer, oesophagus cancer, or breast cancer.

EXAMPLES

Example 1

Analysis in Patients Treated with a FOLFIRI Regimen

The present study included patients treated by a FOLFIRI regimen and aimed to determine genetic and pharmacokinetic factors to tailor 5-FU and irinotecan administrations and determine the impact of individual dose-adjustment in first-line chemotherapy of advanced colorectal cancer.

Genetic factors studied for 5-FU included:

the double polymorphism of TS (Thymidylate synthase), i.e. a 28-base pair tandem repeat sequence within the 5'-untranslated region with a single nucleotide polymorphism (SNP): the presence of a triple repeat (3R) instead of a double repeat (2R) either in heterozygous (2R/3R) or homozygous (3R/3R) configuration has been suggested to increase TS expression and consequently 5-FU sensitivity, thus resulting in potential increased 5-FU efficiency and increased risk of developing toxicities dues to 5-FU administration.

DPD (dihydropyrimidine deshydrogenase) SNPs (IVS 14+1G>A, 2846 A>T, 1679 T>G and 464 T>A): the presence of any of these mutations in the DPD gene increases 5-FU sensitivity and thus potential increased efficiency and the risk of developing toxicities dues to 5-FU administration.

MTHFR (Methylene-tetrahydrofolate reductase) SNPs (677 C>T and 1298 A>C): These mutations cause reduction in enzyme activity, which has been suggested to favour 5-FU cytotoxic activity (and thus potential toxicity).

Genetic factors studied for irinotecan included:

UGT 1A1 (uridine diphosphate glucuronosyltransferase 1A1) polymorphisms (FIG. 1): It has been determined that UGT enzyme levels are regulated primarily through transcriptional control, and that variation in promoter structure influences the rate of transcription. In particular, a series of TA repeats in the proximal promoter vary from five to eight in length: the higher the number of repeats, the less efficient the transcriptional activity of the gene, and the highest the risk of toxicity induced by irinotecan.

The commonest alleles are those with six (6) and seven (7) repeats, so that most patients have a 6/6 (twice 6 repeats), 6/7 (one 6 repeats, and one 7 repeats) or 7/7 (twice 7 repeats) genotype, while some patients may have a 5/6 (one 5 repeats, and one 6 repeats) or 5/7 (one 5 repeats, and one 7 repeats) genotype.

In addition, 2 other UGT1A genotypes (G71R in exon 1 and Y486D in exon 5) are analyzed. These genotypes are present in Asian populations and are responsible for Gilbert syndrome. In Caucasian populations, Gilbert syndrome is due to the above described 7/7 polymorphism (Rouits et al, Clin Cancer Res. 2004 Aug. 1; 10(15):5151-9).

Patients and Methods

Patients

A total of 90 patients were studied. All were treated for advanced colorectal cancer following treatment including irinotecan, fluorouracil and leucovorin (FOLFIRI Regimen)

Other eligibility criteria included first line of treatment

≥18 years of age and with an estimated life expectancy of at least 3 months measurable metastatic lesions
  normal bone marrow and organ function (particularly cardiac function) before the administration of fluorouracil Written informed consent was obtained from all patients before peripheral blood samples were taken for biomolecular analysis.

A computed tomography scan was performed and metastatic lesions were measured prior to beginning treatment then every 3 months.

Initial characteristics of patients are described in following Table 3.

TABLE 3 patients initial characteristics

| Clinical data | | Number of cases | Percentage |
|---|---|---|---|
| Gender | Male | 62 | 69 |
|  | Female | 28 | 31 |
| PS | 0-1 | 86 | 95.5 |
|  | 2-3 | 4 | 4.5 |
| Median age (years) | | 64.5 | |
| Range (years) | | 23-82 | |
| Tumor site | Colon | 69 | 76.6 |
|  | Rectum | 21 | 23.4 |
| Metastatic site | | | |
| Unique site | Liver | 53 | 58.9 |
|  | Lung | 11 | 12.2 |
|  | Peritoneal Carcinomatosis | 6 | 6.7 |
|  | Nodes | 2 | 2.2 |
| Number of sites >1 | | 18 | 20.0 |
| First line of treatment | | 84 | 93.3 |

Treatment

After 200 mg/m$^2$ of intravenous leucovorin bolus and 400 mg/m$^2$ of intravenous push of 5-FU for 10 minutes, 5-FU was administered with an initial dose of 2,500 mg/m$^2$ every two weeks for 46-hours through a battery-operated pump, except in case of DPD significant mutation, in which case the initial dose of 5-FU in 46 hours continuous infusion was decreased by 50%.

The 5-FU dose in 46 hours continuous infusion was then tailored using the method according to the invention, in which 5-FU plasma concentrations were measured after 43 hours (steady-state concentration).

Irinotecan was administered before 5-FU for 2 hours and the initial dose was 180 mg/m$^2$ without reduction for UGT 1A1 7/7 genotype group.

Treatment was continued until documented progression.

Genotyping of Patients

Genomic DNA was isolated in peripheral blood leukocytes.

Figure 1:
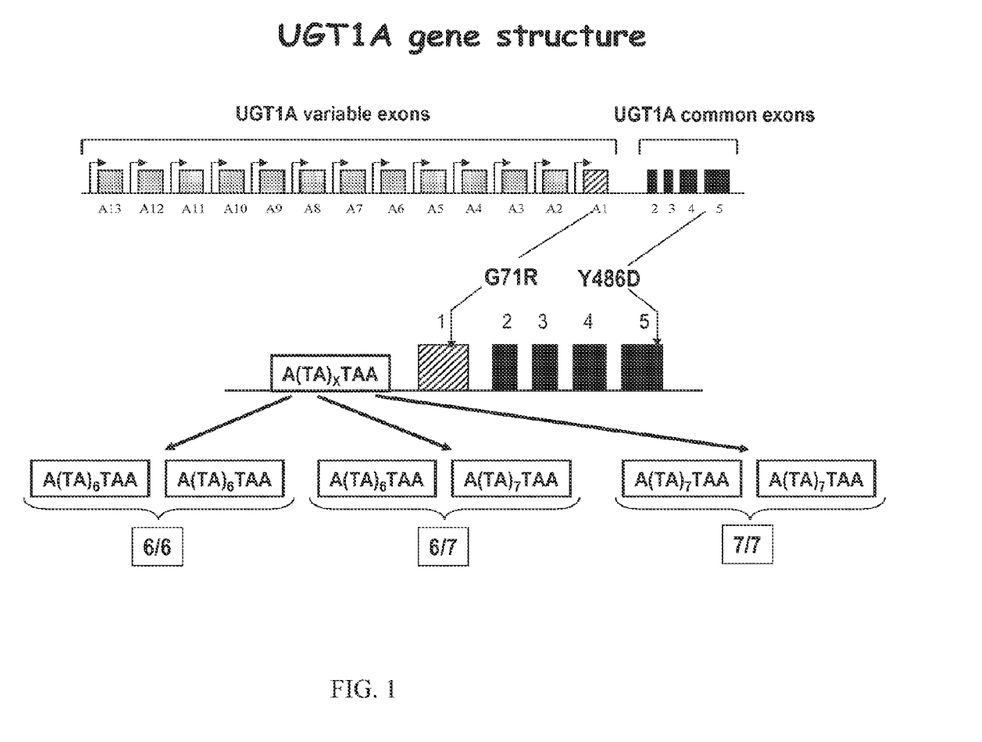
FIG. 1. Structure of human uridine diphosphate-glucuronosyltransferase (UGT) 1A1 gene, containing 13 uridine diphosphateglucuronosyltransferase genes, each consisting of 1 unique exon (1-13) and 4 commons exons (2-5). We indicate the proximal part of the promotor of the UGT1A1 gene which contains a TATA box with the 2 extra nucleotides.

The double polymorphism of TS, i.e. a 28-base pair tandem repeat sequence within the 5'-untranslated region with a single nucleotide polymorphism (SNP), was analysed by PCR and RFLP methods (FIG. 1).

TS expression 'low' or 'high' follows the classification described by Kawakami et al.

DPD SNPs (IVS 14+1G>A, 2846 A>T, 1679 T>G and 464 T>A), MTHFR SNPs (677 C>T and 1298 A>C) and UGT 1A1 polymorphisms (FIG. 1) were investigated by pyrosequencing.

Statistical Analysis

Statistical analysis used the chi2 test, linear regression analysis and the Kaplan-Meier method.

Results

Treatment Administered

Initial 5-FU dose for the 46 Hours Continuous Infusion

Based on the previous detection of a possible increased sensitivity to 5-FU, the initial 5-FU dose for the 46 hours continuous infusion of the first cycle was adapted as follows:

TABLE 5

Adaption of the initital 5-FU dose for the 46 hours continuous infusion

| D (cycle 1) (% of standard) | Number of patients | % of patients |
|---|---|---|
| ≥100 | 77 | 85.5 |
| 50 < D < 100 | 10 | 11.1 |
| ≤50 | 3 | 3.4 |

Optimal 5-FU dose for the 46 Hours Continuous Infusion

Using the adaptation method according to the invention permitting to calculate at each cycle the next 5-FU dose for the 46 hours continuous infusion, the dose of each patient was stabilized to an optimal dose.

The range of obtained optimal doses, expressed as the percentage of the standard dose 2500 mg/m$^2$/cycle, is represented in following Table 6:

TABLE 6

Optimal 5-FU dose for the 46 hours continuous infusion

| Doptimal (% of standard) | Number of patients | % of patients |
|---|---|---|
| <90 | 10 | 11.1 |
| 90 ≤ D ≤ 110 | 42 | 46.7 |
| >110 | 38 | 42.2 |
| >120 | 15 | 16.6 |

Results clearly show that the optimal dose has been changed from the standard dose (±10%) in most patients (53.3%). More precisely, the optimal dose is:
  decreased by more than 10% (optimal dose <2250, 11.1% of patients) or increased by more than 10% (optimal dose >2750, 42.2% of patients) compared to the standard dose in 46.7% of patients. In addition, the optimal dose was increase by more than 20% (optimal dose >3000) compared to the standard dose in 16.6% of patients, which represents a significant proportion of patients.
  more or less equal to the standard dose+/-10% in only 46.7% of patients.

These results highlight the inadequacy of standard doses and thus the importance of the method according to the invention.

Genotyping

Results are displayed in following Table 4

TABLE 4

Distribution of UGT 1A1, TS, DPD and MTHFR polymorphisms

|  |  | Number of patients | Frequency (%) |
|---|---|---|---|
| TS Polymorphisms | 2R/2R | 22 | 24.4 |
|  | 2R/3R | 43 | 47.8 |
|  | 3R/3R | 24 | 26.7 |
|  | 2R/4R | 1 | 1.1 |

TABLE 4-continued

Distribution of UGT 1A1, TS, DPD and MTHFR polymorphisms

|  |  | Number of patients | Frequency (%) |
|---|---|---|---|
| TS Expression | 'high' | 59 | 65.6 |
|  | 'low' | 31 | 34.4 |
| MTHFR 1298 A > C | A/A | 37 | 41.1 |
|  | A/C | 45 | 50.1 |
|  | C/C | 8 | 8.9 |
| MTHFR 677 C > T | C/C | 45 | 50.0 |
|  | C/T | 35 | 38.9 |
|  | T/T | 10 | 11.1 |
| DPD 2846 | A > T | 1 | 1.1 |
| IVS 14 + 1 | G > A | 2 | 2.2 |
| UGT 1A1 | 5/6 | 1 | 1.1 |
|  | 5/7 | 1 | 1.1 |
|  | 6/6 | 37 | 41.1 |
|  | 6/7 | 39 | 43.3 |
|  | 7/7 | 12 | 13.4 |

Thus, 3 patients received an initial dose of 5-FU in 46 hours continuous infusion decreased by 50% compared to the standard dose of 2500 mg/m² due to the presence of a significant mutation in the DPD gene.

Patients with UGT 1A1 7/7 genotype and thus with increased risk of irinotecan toxicity were also present in the group analyzed.

Toxicity

Treatment was globally well tolerated: there were 289 toxic events with 264 graded 1-2 (91.3%) and only 25 graded 3-4 (8.7%).

Irinotecan Mediated Toxicity

UGT 1A1 7/7 genotype group (12 patients, 13.4% in global population) was statistically correlated with a higher risk of toxicity −26.2% grade III-IV neutropenia and diarrhea (p=0.047). This is not surprising since the initial irinotecan dose was not decreased despite detection of UGT 1A1 7/7 genotype and irinotecan dose was not adapted in the course of treatment.

5-FU Mediated Toxicity

In contrast, after initial lower dose (−50%) then adaptation, only 1 neutropenia grade 4 was observed in DPD SNP's group (3%), which is very satisfying for patients with such a mutated impaired DPD gene.

Response Rate

Figure 2:
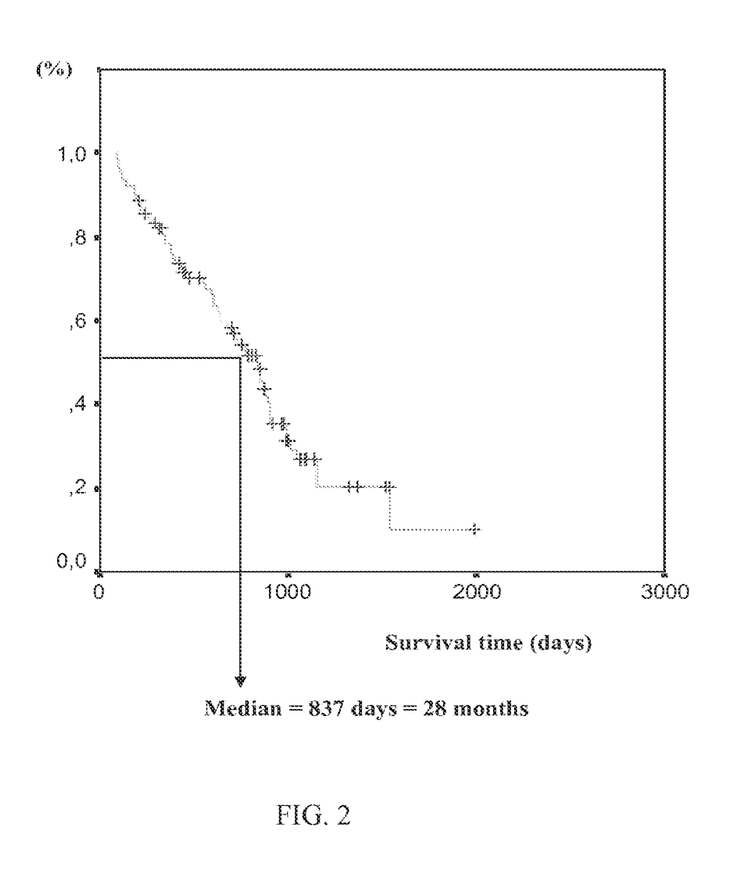
FIG. 2. Kaplan-Meier curve for overall survival with the median at 28 months. The percentage of treated patients alive depending on time is displayed.

The overall response rate was 42.3%, the median overall survival and median progression-free survival times were 28 and 10 months respectively (FIG. 2).

UGT 1A1 7/7 genotype group (12 patients, 13.4% in global population) was also statistically correlated with a shorter response rate to FOLFIRI regimen (16.7%).

The overall survival time of the patients with 3R/3R TS genotype associated with C/C for 677 C>T or A/A for 1298A>C (20 patients=22.2%) was not statistically less than that of the patients with another genotype, as previously observed with regimen including only 5-FU and leucovorin.

Discussion

This study analysed both DPD, TS, MTHFR and UGT 1A1 polymorphisms in a homogeneous cohort of 90 patients with advanced colorectal cancer treated with fluorouracil, leucovorin and irinotecan (FOLFIRI regimen).

With pharmacokinetic dose adaptation for 5-FU, this treatment was efficient and well tolerated thanks to 5-FU dose adjustment that lowered the incidence of severe toxic side-effects compared to usual FOLFIRI regimens without 5-FU dose adaptation.

In addition, the adaptation method according to the invention permitted to significantly increase 5-FU dose in a significant number of patients without increasing toxicity, thus permitting a more efficient treatment than using standard doses.

In conclusion, DPD SNP's genotyping combined to individual dose-adjustment with pharmacokinetic follow-up permits to significantly improve FOLFIRI regimens by optimizing response rate and decreasing severe adverse side effects.

Example 2

Analysis in Patients Treated with a FOLFIRI+Cetuximab Regimen

Patients and Methods

Patients 90 patients under 80 years with a metastatic colorectal adenocarcinoma in $2^{nd}$ then amended to $1^{st}$ line chemotherapy (jul 2007), PS≤2, normal organ function. No total DPD deficiency.

Treatment

Cetuximab: standard dose (400 mg/m²D1) then 250 mg/m² weekly.

After 200 mg/m² of intravenous leucovorin bolus and 400 mg/m² of intravenous push of 5-FU for 10 minutes, 5-FU was administered with an initial dose of 2,500 mg/m² (+/−10%, i.e. 2200-2800 mg/m²) every two weeks for 46-hours through a battery-operated pump, except in case of 5-FU increased sensitivity, in which case the initial dose of 5-FU in 46 hours continuous infusion was decreased by 50%. In an old patient without observed increased 5-FU sensitivity, the clinician decided to decrease 5-FU dose despite absence of observed increased 5-FU sensitivity.

The 5-FU dose in 46 hours continuous infusion was then tailored using the method according to the invention, in which 5-FU plasma concentrations were measured after 43 hours (steady-state concentration).

Irinotecan was administered before 5-FU for 2 hours at a dose comprised between 70 and 340 mg/m².

Treatment was continued until documented progression.

Genotyping of Patients

Was performed as described in Example 1.

Results

Increased 5-FU Sensitivity and Initial 5-FU Dose

DPD mutations were searched and $UH_2/U$ ratios calculated. Four patients were found to have increased 5-FU sensitivity:

2 patients had a DPD mutation and UH2/U ratios of 6.5 and 5.9 respectively.

2 patients did not have a DPD mutation but displayed a $UH_2/U$ ratio of 5.4.

The initial 5-FU dose was decreased of 25-50% in these patients (4.4% of all patients) as described in the general description.

Final 5-FU Dose

After following the adaptation method according to the invention, it was found that the final 5-FU dose was:

equal to the standard dose 2,500 mg/m² (+/−10%, i.e. 2200-2800 mg/m²) in 58 patients (64.4%), adapted (increased or decreased) by more than 10% compared to the standard dose in 32 patients (35.6%), with the following pattern:

final dose increased by more than 10% compared to standard dose: 16 patients (17.8%). In these patients, administration of the standard dose would probably have resulted in decreased treatment efficiency.

final dose decreased by more than 10% compared to standard dose: 16 patients (17.8%). In these patients, using the standard dose would most probably have resulted in serious toxicities.

These results once more highlight the inadequacy of standard doses and thus the importance of the method according to the invention.

Conclusion

The above results clearly show that the method according to the invention is also useful and adapted in FOLFIRI regimens further comprising cetuximab treatment.

BIBLIOGRAPHY

Douillard, J. Y., Cunningham, D., Roth, A. D., et al: Irinotecan combined with fluorouracil compared with fluorouracil alone as first-line treatment for metastatic colorectal cancer: a multicentre randomised trial. Lancet 355: 1041-1047, 2000

EP 1 712 643

Etienne M C, Lagrange J L, Dassonville O, et al: Population study of dihydropyrimidine dehydrogenase in cancer patients. J Clin Oncol 12: 2248-2253, 1994

Gamelin E., Boisdron-Celle M., Guérin-Meyer V., Delva R., Lortholary A., Genevieve F., Lana F., Ifrah N., Robert J. Correlation between uracil and dihydrouracil plasma ratio, and 5-fluorouracil pharmacokinetic parameters and tolerance in patients with advanced colorectal cancer. A potential interest for predicting 5-FU toxicity and for determining optimal 5-FU dosage. J Clin Oncol, 1999, 17, 1105-1110

Gamelin E., Boisdron-Celle M., Delva R., Regimbeau C., Cailleux P. E., Alleaume C., Maillet M. L., Goudier M. J., Sire M., et al. Long-term weekly treatment of colorectal metastatic cancer with fluorouracil and leucovorin: results of a multicentric prospective trial of fluorouracil dosage optimization by pharmacokinetic monitoring in 152 patients. J. Clin. Oncol., 1998, 16 (4), 1470-1478

Gamelin E., Boisdron-Celle M. Dose monitoring of 5-fluorouracil in patients with colorectal or head and neck cancer. Status of the art. Crit Rev Oncol Hematol, 1999, 30, 71-79

Gamelin E, Delva R, Jacob J, Merrouche Y, Raoul J L, Pezet D, Dorval E, Piot G, Morel A, Boisdron-Celle M. Individual fluorouracil dose adjustment based on pharmacokinetic follow-up compared with conventional dosage: results of a multicenter randomized trial of patients with metastatic colorectal cancer. J Clin Oncol. 2008 May 1; 26(13):2099-105.

Rouits E et al. Relevance of different UGT1A1 polymorphisms in irinotecan-induced toxicity: a molecular and clinical study of 75 patients. Clin Cancer Res. 2004 Aug. 1; 10(15):5151-9.

Vanhoefer, U., Harstrick, A., Achterrath, W., Cao, S., Seeber, S., and Rustum, Y. M. Irinotecan in the treatment of colorectal cancer: clinical overview. J. Clin. Oncol., 19: 1501-1518, 2001.

Ychou M, Duffour J, Kramar A, et al. Individual 5-FU adaptation in metastatic colorectalo cancer: results of a phase II study using a bimonthly pharmacokinetically intensified LV5FU2 regimen. Cancer Chemother Pharmacol, 2003, 52: 282-90.

The invention claimed is:

1. A method for treating a cancer patient in need thereof, said method comprising the steps of:

a. determining from a blood sample of a patient suffering from cancer the dose $D(n+1)$ of 5-fluorouracile (5-FU) for the next cycle of treatment (n+1), wherein each treatment cycle n comprises:

0-500 mg/m2 of 5-FU administered in a bolus, 0-600 mg/m2 of folinic acid or a salt thereof, a dose $D(n)$ (in $mg/m^2$) of 5-FU administered in a continuous infusion of 43 to 49 hours, and 0-500 $mg/m^2$ of irinotecan; and said blood sample has been taken from said patient in previous treatment cycle n at least 1 hour after the beginning of the 5-FU perfusion and before the end of said perfusion, said method comprising:

measuring in vitro the 5-FU plasmatic concentration in the blood sample calculating $D(n+1)$ depending on $D(n)$ using the following decision scheme:

if [5-FU]<100 µg/L, then $D(n+1)=D(n)\times 1.40$, if 100<[5-FU]<200 µg/L, then $D(n+1)=D(n)\times 1.30$, if 200<[5-FU]<300 µg/L, then $D(n+1)=D(n)\times 1.20$, if 300<[5-FU]<400 µg/L, then $D(n+1)=D(n)\times 1.10$, if 400<[5-FU]<500 µg/L, then $D(n+1)=D(n)\times 1.05$, if 500<[5-FU]<600 µg/L, then $D(n+1)=D(n)\times 1.025$, if 600<[5-FU]<650 µg/L, then $D(n+1)=D(n)$, if 650<[5-FU]<700 µg/L, then $D(n+1)=D(n)\times 0.975$, if 700<[5-FU]<800 µg/L, then $D(n+1)=D(n)\times 0.95$, if 800<[5-FU]<900 µg/L, then $D(n+1)=D(n)\times 0.90$, if >900 [5-FU], then $D(n+1)=D(n)\times 0.80$, and b. administering the dose $D(n+1)$ calculated in step a) to the patient.

2. The method according to claim 1, wherein the duration of the continuous infusion of 5-FU in each cycle n is about 46 hours.

3. The method according to claim 1, wherein the dose of 5-FU administered in a bolus in each cycle n is about 400 $mg/m^2$.

4. The method according to claim 1, wherein the dose of folinic acid or salt thereof administered to the patient in each cycle n is about 100 $mg/m^2$.

5. The method according to claim 1, wherein the dose of irinotecan administered to the patient in each cycle n is comprised between 120 and 300 $mg/m^2$.

6. The method according to claim 1, wherein the treatment further comprises the administration to the patient in each cycle n of an anticancer monoclonal antibody.

7. The method according to claim 6, wherein said anticancer monoclonal antibody is cetuximab, panitumumab or bevacizumab.

8. The method according to claim 1, wherein the blood sample has been taken in cycle n 15 minutes to 22 hours before the end of the 5-FU continuous infusion.

9. The method according to claim 8, wherein the blood sample has been taken in cycle n 2 to 3 hours before the end of the 5-FU continuous infusion.

10. The method according to claim 1, wherein the blood sample has been taken in cycle n between 1 hour and 5 hours after the beginning of the 5-FU continuous infusion.

11. The method according to claim 1, comprising pre-treatment diagnosis of a possible increased sensitivity of said patient to 5-FU, and wherein the 5-FU dose $D(n)$ administered in a continuous infusion in cycle n is at most about 2500 $mg/m^2$ and has been determined based on the pre-treatment diagnosis.

12. The method according to claim 11, wherein the diagnosis of a possible hypersensitivity of said patient to 5-FU is performed from at least one biological sample of said patient by combining at least two of the following in vitro tests:
  a) the analysis of the presence of a significant mutation in DPD gene,
  b) the measure of uracil plasmatic concentration, and
  c) the measure of the ratio dihydrouracil plasmatic concentrations/uracil plasmatic concentration ($UH_2/U$ ratio).

13. The method according to claim 12, wherein the three in vitro test have been performed and the initial dose D(n) has been determined using the following decision algorithm:
  a) If
    no significant mutation in DPD gene has been detected and uracil plasmatic concentration is less than 15 gg/L, or
    no significant mutation in DPD gene has been detected and uracil plasmatic concentration is at least 15 p.g/L but the UH2/U ratio is at least 6,
  then a standard dose D(n) of 2500 mg/m2 is administered to the patient in cycle n;
  b) In all other cases,
    if 6<UH2/U ratio, then D(n) is 1750 mg/m$^2$
    if 3<UH2/U ratio<6, then D(n) is 1250 mg/m$^2$
    if 1<UH2/U ratio<3, then D(n) is 750 mg/m$^2$
    if $UH_2/U$ ratio<1 then the patient is preferably not treated with 5-FU.

14. The method according to claim 1, wherein said patient is suffering from colorectal cancer, stomach cancer, hepatic ducts cancer, pancreas cancer, oesophagus cancer, or breast cancer.

* * * * *